(12) United States Patent
Lasner et al.

(10) Patent No.: US 12,310,612 B2
(45) Date of Patent: May 27, 2025

(54) ATRAUMATIC PRONG FORCEPS

(71) Applicants: Jeffrey I Lasner, Boynton Beach, FL (US); Michael E Lasner, Mt Kisco, NY (US); Daniel M Lasner, White Plains, NY (US)

(72) Inventors: Jeffrey I Lasner, Boynton Beach, FL (US); Michael E Lasner, Mt Kisco, NY (US); Daniel M Lasner, White Plains, NY (US)

( * ) Notice: Subject to any disclaimer, the term of this patent is extended or adjusted under 35 U.S.C. 154(b) by 315 days.

(21) Appl. No.: 17/899,425

(22) Filed: Aug. 30, 2022

(65) Prior Publication Data
US 2024/0065715 A1 Feb. 29, 2024

(51) Int. Cl.
*A61B 17/29* (2006.01)

(52) U.S. Cl.
CPC ...... *A61B 17/29* (2013.01); *A61B 2017/2905* (2013.01); *A61B 2017/2946* (2013.01)

(58) Field of Classification Search
CPC ............. A61B 17/2812; A61B 17/282; A61B 17/2841; A61B 17/29; A61B 17/2833; A61B 17/28; A61B 17/30; A61B 2017/2845; A61B 2017/2905; A61B 2017/2946; A61B 2017/2904; A61B 2017/2926; A61B 2017/305
See application file for complete search history.

(56) References Cited

U.S. PATENT DOCUMENTS

| | | | | |
|---|---|---|---|---|
| 1,679,497 | A * | 8/1928 | Reeves | A61B 17/32056 606/118 |
| 3,391,690 | A * | 7/1968 | Thomas | A61B 17/2812 83/171 |
| 4,823,792 | A * | 4/1989 | Dulebohn | A61B 17/2812 606/208 |
| 6,793,208 | B1 * | 9/2004 | Riddle, Jr. | G02C 13/001 269/6 |
| 2010/0318102 | A1 * | 12/2010 | Cheng | A61B 17/062 606/139 |
| 2013/0247333 | A1 * | 9/2013 | Bender | B25G 1/02 29/527.1 |
| 2018/0153535 | A1 * | 6/2018 | Lasner | A61B 17/00234 |

* cited by examiner

*Primary Examiner* — Jocelin C Tanner
(74) *Attorney, Agent, or Firm* — Joseph M Fowler

(57) ABSTRACT

An atraumatic, scissor-type, surgical forceps is disclosed which incorporates a pair of flat jaws pivotally connected and opposite one another. One or more prongs project from the surface of one flat jaw toward the opposite jaw of the forceps which is without prongs. The jaws are connected to a handle made from flexibly resilient sheet metal which by design limits damage to biological tissue during surgical procedures by preventing the prongs from fully penetrating the tissue.

4 Claims, 5 Drawing Sheets

ATRAUMATIC PRONG FORCEPS

CROSS-REFERENCE TO RELATED APPLICATIONS

The present application claims the benefit of U.S. Provisional Application No. 63/360,095 filed on Aug. 31, 2021, and to U.S. Provisional Application No. 63/372,956 file on Apr. 18, 2022, which are expressly incorporated herein in their entirety by reference thereto.

In addition, U.S. Pat. Nos. 4,527,331; 6,592,603; 7,497,867; 10,499,943 B2 and 10,765,413 B2 are expressly incorporated herein in their entireties by reference thereto.

FIELD OF THE INVENTION

The present invention relates to medical forceps and particularly to surgical forceps that medical professionals use in all aspects of manual medical, veterinary, and dental surgery.

BACKGROUND OF THE INVENTION

Surgical forceps are mechanical instruments used to hold small objects or biological tissue facilitating the performance of specific tasks during operative procedures. Common surgical forceps are made in the form of tweezers or are designed having a scissors action depending on the surgical requirement. Adson forceps and DeBakey forceps are examples of tweezer forceps. During surgery the forceps may be used to move, drag, or "reflect"—fold back—tissue adjacent to an incision. Some forceps employ opposing teeth to keep the membrane or tissue gripped firmly. The manual pressure applied to the handles of the forceps is transferred directly to the working end of the instrument which squeezes the tissue reflected. Great care must be exercised on the part of the clinician to avoid damaging the tissue as it is moved, squeezed or otherwise manipulated. "Atraumatic" forceps are designed to minimize damage to innocent tissue during these clamping or gripping procedures. One approach, illustrated by a DeBakey "atraumatic" tweezer forceps, is to minimize the area of surface tissue gripped between the ends of thin tweezers. Another common type of forceps employs a scissors principle. The jaws on the working end of the scissors forceps can be closed and locked in place using a toothed interlock located near finger loops on the handle end of the forceps. The jaw regions on the working end of scissors forceps can be fixedly clamped on opposite surfaces of the tissue. Consequently, the clamped tissue is subject to continuous external pressure on both internal (hypodermal) and external (epidermal) surfaces. Frequent movement and manipulation of forceps during surgical procedures as well as frequent clamping and unclamping fatigues a clinician and may bruise a wide area of tissue. The weight of the forceps itself can pull or drag on edges of an incision causing fraying or shredding of tissue making the reparative process of suturing more difficult. Unintended damage can also occur due to the application of excessive crushing or tearing which restricts internal blood flow within the tissue causing iatrogenic injury to the patient.

BRIEF SUMMARY OF THE INVENTION

The present invention describes a scissors style surgical forceps constructed from flexibly resilient sheet metal as distinct from most conventional forceps which are forged, cast, machined from solid material, or, possibly, 3D printed. The inventive scissors forceps have a handle end and a working end. The surgical forceps are comprised of flexibly resistant sheet metal components pivotally connected to a pair of flat, opposable jaws which are located on the working end. One of the flat jaws is provided with at least one sharp prong. The prong projects from the surface of the flat jaw toward the opposite flat jaw which is without prongs. In use, the surgeon clinician slides the open jaws of the forceps over upper and lower tissue surfaces bringing the tissue into contact with the sharp prong. Pressing on the handles of the forceps cause the jaws to close allowing the prong to grip or partly penetrate the tissue. This surgical method restricts forceable contact with the tissue to the actual surface area of the sharp prong. The remaining surface area of the tissue which is contained between the flat jaws of the forceps is held gently in position by its own weight and by limited frictional contact with the flat jaw surfaces.

Accordingly, one object of this invention is to provide a surgical forceps which minimizes tissue damage by minimizing the area of forceable contact with the tissue while simultaneously providing an effective grip on tissue manipulated during surgical procedures.

Another object of a preferred embodiment of the invention is to provide a surgical forceps with a single prong which permits the forceps to rotate when locked in a closed jaw configuration and not cause injury to the tissue contained by the jaws when the forceps are rotated.

An object of another embodiment of the invention is to provide a surgical forceps with multiple prongs to make positive fixed placement of tissue during a surgical procedure while limiting forceable surface contact with tissue to the areas indented by the prongs.

Yet another object of the invention is to provide a surgical forceps which engages tissue by means of one of more sharp prongs in which the prongs are prevented from fully penetrating the tissue when the forceps is engaged in a locked or closed condition.

Another object of the invention is to provide lightweight surgical forceps made from flexibly resilient sheet metals which are less burdensome to use during lengthy surgical procedures.

Another object of the invention is to provide forceps which minimizes the likelihood that tissue becomes frayed during surgical manipulation.

Various other features, objects and advantages of the present invention will become apparent from the following description taken with reference to the accompanying drawings.

DETAILED DESCRIPTION OF THE INVENTION

Figure 1:
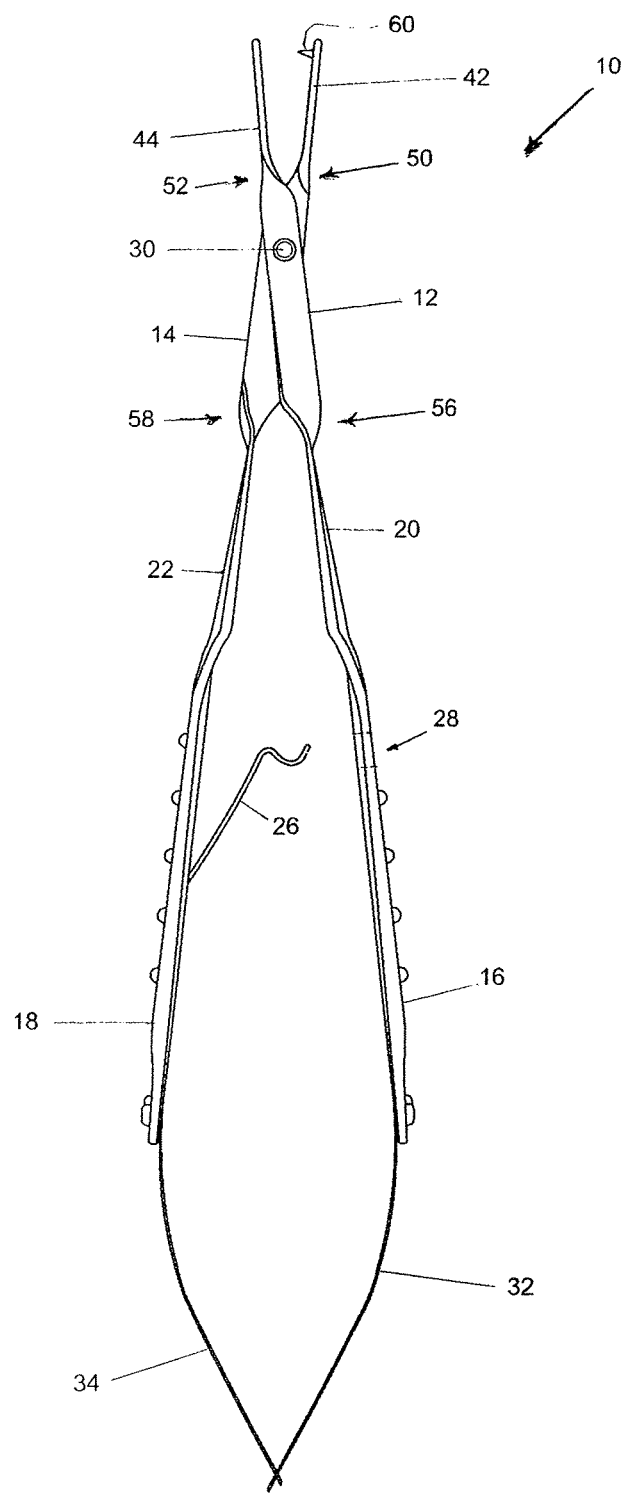
FIG. 1 is a side elevation of a preferred embodiment of the inventive surgical forceps having a single prong in which the jaws are maintained fully open and unlocked with the handles separated by means of leaf springs.
Figure 2:
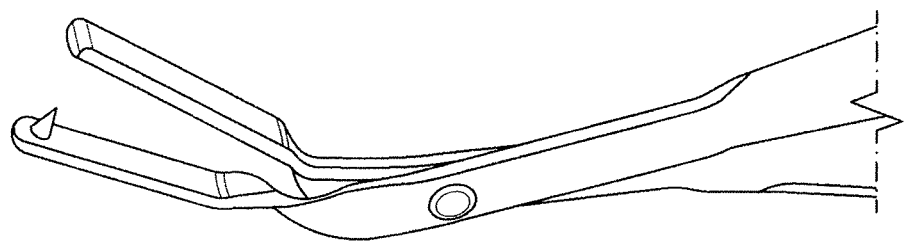
FIG. 2 is a scaled perspective view of the working end of the forceps shown in FIG. 3 having a single prong and flat opposable pair of jaws bent offset from the central axis of the forceps instrument.
Figure 3:
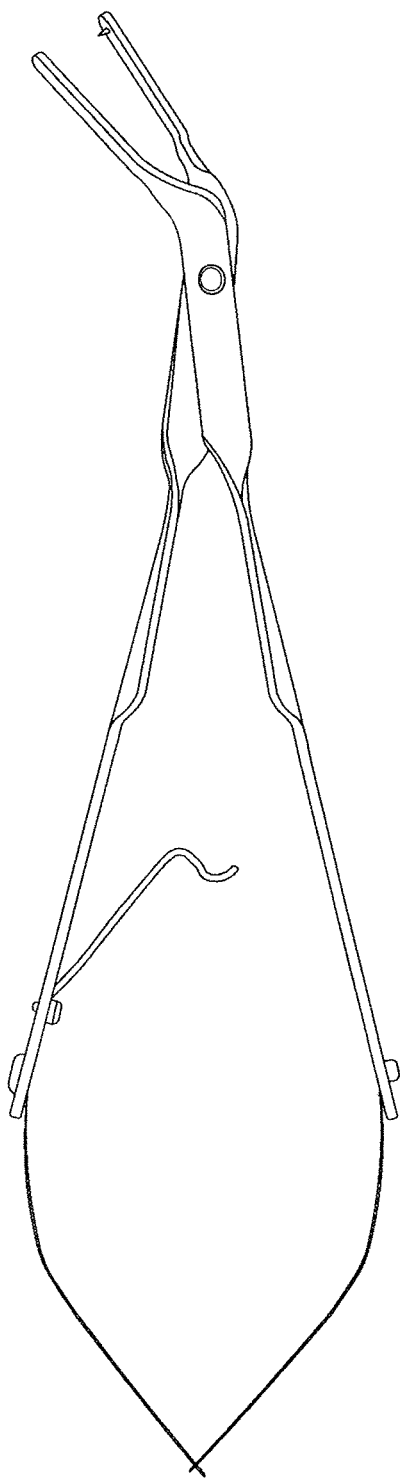
FIG. 3 is a side elevation of a second embodiment of the inventive surgical forceps identical to the forceps in FIG. 1 except the flat opposable jaws are bent offset at an angle with respect to the central axis of the forceps instrument.

FIG. 1 of the drawings depicts a scissors type surgical forceps 10 of a kind used to hold objects or biological tissues including membranous tissue, muscle, or bone during microsurgical procedures. The forceps in FIG. 1 are comprised of a pair of sheet metal components 12 and 14 extending longitudinally to shank components 20 and 22 respectively, which extend to and are integral with handle portions 16 and 18 respectively. The sheet metal components 12 and 14 are pivotally connected by a mechanical fastener at point 30 to form an assembled scissors mechanism. Each of the paired components 12 and 14 is oriented to complement the other component and are mechanically aligned and mated to create the scissors forceps assembly 10.

The inventive scissors forceps has a handle end and a working end. Each embodiment of the inventive forceps described herein and shown in the enumerated FIGS. has an identical handle end. Therefore, to avoid confusion and duplication, the reference numerals are similar for each handle. Leaf springs, 32 and 34, are located at one end of each handle. The springs provide biasing means to keep the handles separated. The leaf springs 32,34 are interlocked at the end opposite their individual attachments to each handle. The handle of the present invention is described more comprehensively in Lasners' U.S. Pat. No. 10,765,413 (2020) which has been adapted, in part, as the handle for the present inventive forceps. However, the locking device described for the handle in that prior patent is different from the locking device for the handle described in this current application.

The working end of the scissors forceps as shown in FIG. 1 extends forward from a pivot point 30 or fulcrum to form a pair of overlapping flat jaws 42 and 44. The jaws, 42 and 44, are oppositely positioned, overlapping, and pivotable toward and away from one another. The flat jaws 42 and 44 are formed by a 90-degree twist in portions 52 and 50 respectively of the sheet metal components 12 and 14 forward of pivot point 30 near the extended ends of components 12 and 14.

A second 90-degree twist in the sheet metal, rearward of pivot point 30, between the handle end and the working end of the forceps enables the formation of a hard mechanical stop. The hard stop is created by an interference between components 12 and 14 at portions 56 and 58 respectively, which limits the closing distance between jaws 42 and 44 when the jaws of the scissors forceps are fully closed.

Figure 4:
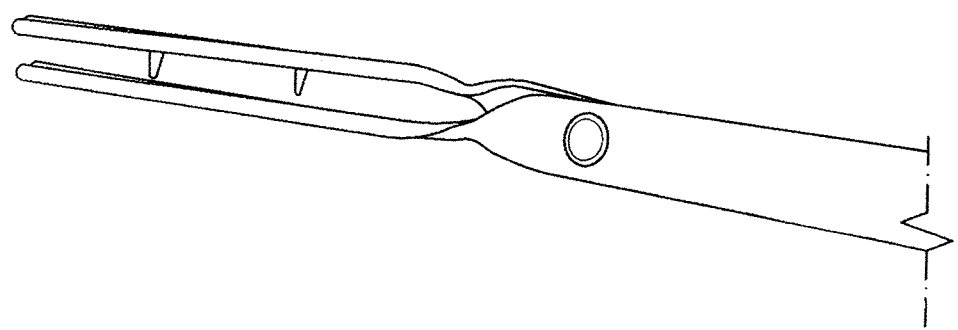
FIG. 4 is a scaled side elevation of the working end of a third embodiment of the forceps of the shown in FIG. 1 equipped with two prongs for tissue engagement mounted in line on a flat jaw surface.

At least one prong 60 is fixed perpendicularly on one of the flat surfaces of the pair of forceps jaws. The prong tapers to a point in the direction of the opposite jaw surface. The prong 60 is typically conical in shape and joined at its base to the flat surface on the jaw. A multiplicity of similar prongs may be provided in other embodiments of the invention to address particular surgical requirements. For example, a partial view of an embodiment of the jaws of the surgical forceps in FIG. 4 depicts two prongs spaced apart, in line, opposing a flat jaw thereby enabling wider tissue grip.

In use, a clinician moves the working end of the forceps with its open jaws forward over the edge of tissue involved in a procedure. The tissue is supported between the flat regions on the jaws as it is maneuvered or gripped. When the clinician presses the forceps handles together causing the jaws to close, the sharp point of a prong engages one side of the tissue. Notably, most of the tissue present or contained within the jaw space is not directly subject to the force exerted by the prong. The surface area of a pointed prong (or prongs) is very small compared to the area of tissue and relatively small compared to the total surface area of the flat jaws of the forceps. Consequently, a relatively small gripping force is directed into the tissue. If the clinician presses too hard, that force is limited by the flexibly resilient sheet metal handles and the hard stop limits the extent to which the prong can approach the opposite flat jaw and the tissue as it is pressed against the flat jaw surface. The elastic deformation on the pointed apex of the prong is not permitted to exceed the fracture limit of the tissue membrane as it is stretched, moved or indented by the prong.

Prior efforts to create atraumatic forceps minimize surface area be providing very narrow jaw dimensions and enhance gripping force with opposing teeth or roughened surfaces. The current inventive forceps relies on the prong forcing the tissue against a wider flat surface which has proven more effective and less damaging to surrounding tissue. This is especially true when, as in most surgical proceedings, multiple instruments may be employed at different times during the process. Forceps may be locked in position and then moved while additional clamps and forceps are employed. A particular advantage of the single prong inventive scissors forceps is that it can be adapted to allow the prong to penetrate the tissue and still create a small space between the tissue below the opposite flat jaw. As such, the forceps, with its conically shaped prong, can be rotated without doing any tissue damage and without having to be unlocked, repositioned, and relocked. A toothed or wide contact surgical forceps can't be rotated without the risk of injuring a wide area of tissue; it must be mechanically released before repositioning and relocking.

In use, the prong only has a mild impact, if any, on the flat surface of the opposite jaw as, at a minimum, a space remains for the thickness of the tissue. Different types of surgery require the inventive forceps to have different closing and locking characteristics. The height of the prong may vary and the distance between prongs—if multiple prongs are required—must be suitably adapted to the type of surgery and tissues engaged. Various tensioning members of the flexibly resilient steel components including the hard stop may be controlled or modified for different surgical conditions.

Figure 7:
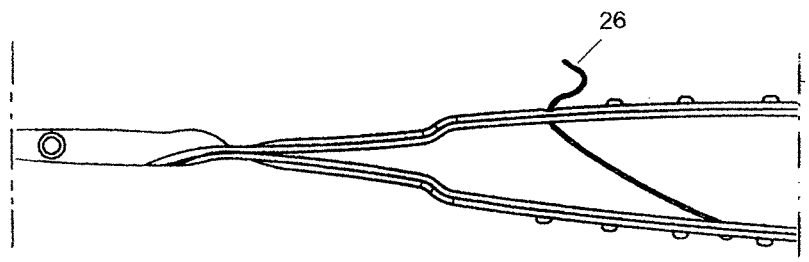
FIG. 7 is a side elevation of the handle portion of the surgical forceps of FIG. 1 positioned horizontally and rotated to show the handle latching mechanism when the handles are closed and locked.
Figure 6:
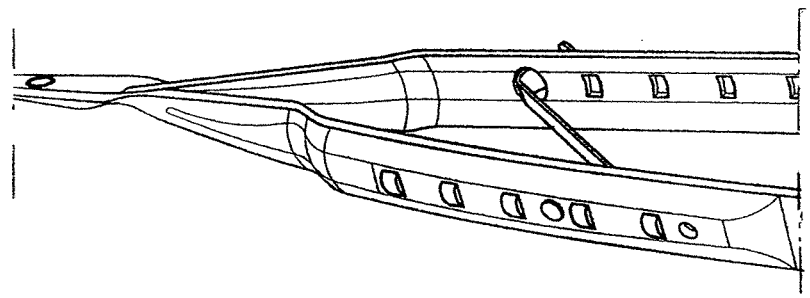
FIG. 6 is a perspective view of the handle portion of the surgical forceps of FIG. 1 positioned horizontally and rotated to show the handle latching mechanism when the handles are closed and locked.
Figure 5:
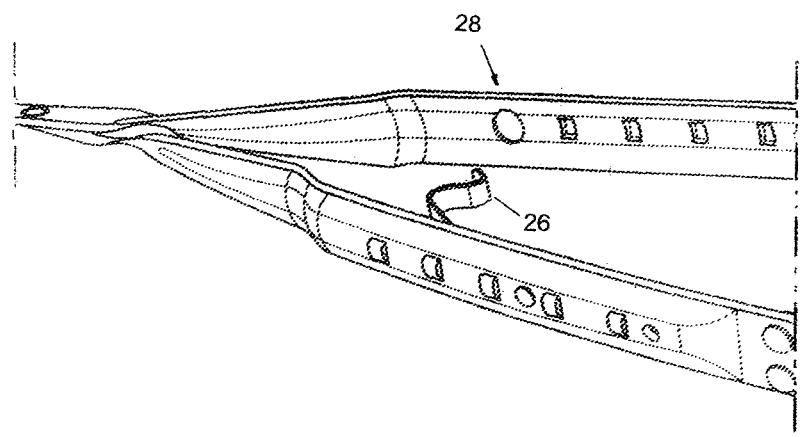
FIG. 5 is a perspective view of the handle portion of the surgical forceps of FIG. 1 positioned horizontally and rotated to show the handle latching mechanism when the handles are open and unlocked.

The forceps can be locked in place on the tissue during a surgical procedure. The locking device for the scissors forceps 10 shown in FIG. 1 comprises a springy link 26 fixed to an interior side of a first handle 18 extending toward the interior side of a second handle 16. An aperture 28 in second handle 16 as shown in FIG. 6 and FIG. 7 is designed to receive the inverted S-shaped end of the springy link 26 when the forceps are closed. When the clinician squeezes the handles together the curved S-shaped end of link 26 is intercepted by the lower edge of aperture 28 in second handle 16 as the forceps are closing. This movement forces the springy link backwards, slightly compressing it, while simultaneously pushing it forward into and through aperture 28. When the S-shaped end of the link is forced through aperture 28 onto the outer surface of handle 16, the forceps are locked closed as in FIG. 7. The forceps remain closed until the surgeon clinician, using slight thumb pressure, pushes the "S" portion of link 26 forward toward the open portion of aperture 28 allowing leaf springs 32,34 to rebound forcing the handles open again releasing the forceps hold on the tissue.

This simple latching arrangement for the inventive forceps reduces finger and hand tension for the clinician during long surgery sessions. Many conventional scissors-type locking forceps require the engagement of ratchet teeth near the ring handles of the instrument. The forceps handles are pressed to engage the teeth and require a sideways motion of fingers holding the forceps to release the teeth. The present invention employs more natural and intuitive hand movements: Press to lock the forceps. Move the thumb forward to unlock. The clinician's thumb is normally in position holding the handle of the instrument ready to disengage the lock. No sideways pushing or urging motion is required of the clinician's secondary fingers holding the forceps.

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed.

We claim:

1. A surgical scissors forceps comprising:
   a pair of flexibly resilient sheet metal components which are pivotally connected and oriented to complement each other and are mechanically aligned and mated to create a scissors forceps assembly,
   said scissors forceps having a working end and a handle end, and
   the working end extends forward from a pivot point where portions of said pair of flexibly resilient sheet metal components are twisted 90 degrees to form a pair of flat overlapping jaws, and
   one flat jaw of the pair of flat overlapping jaws is provided with at least one discrete, centrally located, sharp prong which projects from the middle of the surface of said flat jaw toward an opposite flat jaw of the pair of flat overlapping jaws which is without prongs, and
   said pair of flat jaws are oppositely positioned, overlapping, and pivotable toward and away from one another.

2. The surgical scissors forceps of claim 1 in which the at least one sharp prong is conically shaped.

3. The surgical scissors forceps of claim 2 in which a hard mechanical stop formed by 90-degree twists in portions of said pair of flexibly resilient sheet metal components, rearward and forward of the pivot point limits the extent to which a sharp prong can approach the opposite flat jaw which is without prongs.

4. The surgical scissors forceps of claim 3 having a locking device on a handle end comprising:
   two interlocking leaf springs,
   a first handle and a second handle,
   a springy link fixed to an interior side of a first handle having a distal inverted S-shaped end extending toward the interior side of a second handle,
   an aperture in the second handle designed to receive the distal inverted S-shaped end of the springy link when the first handle and the second handle of the forceps are closing,
   aforesaid leaf springs biasing the distal inverted S-shaped end of the springy link into and through the aperture into a locked condition onto the outer surface of the second handle when the first handle and the second handle of the forceps are closed.

\* \* \* \* \*